(12) United States Patent
Murdeshwar et al.

(10) Patent No.: US 11,065,150 B2
(45) Date of Patent: Jul. 20, 2021

(54) DUAL BALLOON FLUID ENDOMETRIAL TREATMENT OF UTERINE TISSUE

(71) Applicant: Gyrus ACMI, Inc., Southborough, MA (US)

(72) Inventors: Nikhil Murdeshwar, Maple Grove, MN (US); Kester J. Batchelor, Mound, MN (US)

(73) Assignee: Gyrus Acmi, Inc., Westborough, MA (US)

( * ) Notice: Subject to any disclaimer, the term of this patent is extended or adjusted under 35 U.S.C. 154(b) by 448 days.

(21) Appl. No.: 15/924,590

(22) Filed: Mar. 19, 2018

(65) Prior Publication Data

US 2019/0282396 A1     Sep. 19, 2019

(51) Int. Cl.
| | |
|---|---|
| A61F 7/12 | (2006.01) |
| A61B 18/02 | (2006.01) |
| A61B 18/00 | (2006.01) |
| A61B 5/00 | (2006.01) |

(52) U.S. Cl.
CPC .............. *A61F 7/123* (2013.01); *A61B 18/02* (2013.01); *A61B 5/4325* (2013.01); *A61B 2018/00017* (2013.01); *A61B 2018/0022* (2013.01); *A61B 2018/00559* (2013.01); *A61B 2018/00791* (2013.01); *A61B 2018/0212* (2013.01); *A61B 2018/0262* (2013.01)

(58) Field of Classification Search
CPC .... A61F 7/123; A61F 7/12; A61F 2007/0054; A61F 2007/0056; A61B 18/02; A61B 5/4325; A61B 2018/00017; A61B 2018/0022; A61B 2018/00255; A61B 2018/0025; A61B 2018/0212; A61B 2018/0262; A61B 2019/00005; A61B 2019/00011; A61B 2019/00017; A61B 2019/00023; A61B 2019/00166; A61B 2019/00214; A61B 2019/025; A61B 2019/0256; A61B 2019/0268
See application file for complete search history.

(56) References Cited

U.S. PATENT DOCUMENTS

| | | | | |
|---|---|---|---|---|
| 6,066,132 | A | * | 5/2000 | Chen ...................... A61B 18/08 604/530 |
| 6,648,879 | B2 | * | 11/2003 | Joye ....................... A61B 18/02 128/898 |
| 9,050,074 | B2 | * | 6/2015 | Joye ....................... A61B 18/02 |
| 9,510,887 | B2 | | 12/2016 | Burnett et al. |
| 9,517,100 | B2 | | 12/2016 | Burnett et al. |
| 2006/0270982 | A1 | * | 11/2006 | Mihalik ................. A61B 18/02 604/113 |

(Continued)

*Primary Examiner* — Ronald Hupczey, Jr.
(74) *Attorney, Agent, or Firm* — Schwegman Lundberg & Woessner, P.A.

(57) ABSTRACT

A medical device includes: a shaft having a distal end and an associated exhaust channel; a first balloon configured to be attached to the distal end of the shaft, the first balloon having an outer surface that is substantially conformal to an inner surface of a uterine cavity; and a second balloon configured to be received within the first balloon and forming an intermediary space between the first balloon and an outer surface of the second balloon. The second balloon includes at least one rupture valve configured to rupture at a predefined pressure in the intermediary space.

22 Claims, 5 Drawing Sheets

(56) References Cited

U.S. PATENT DOCUMENTS

| | | | |
|---|---|---|---|
| 2007/0239110 A1* | 10/2007 | Shah | A61M 25/1011 604/96.01 |
| 2008/0243103 A1 | 10/2008 | Whetham et al. | |
| 2014/0088579 A1* | 3/2014 | Burnett | A61B 18/04 606/21 |
| 2014/0221732 A1* | 8/2014 | Dayton | A61B 17/70 600/30 |
| 2016/0302841 A1* | 10/2016 | Williams | A61B 18/02 |
| 2016/0302868 A1* | 10/2016 | Nagale | A61B 18/24 |
| 2017/0112559 A1 | 4/2017 | Sylliaasen et al. | |

* cited by examiner

DUAL BALLOON FLUID ENDOMETRIAL TREATMENT OF UTERINE TISSUE

BACKGROUND

Field of the Invention

The exemplary and non-limiting embodiments described herein relate generally to devices and methods that relate to procedures for the treatment of uterine tissue. The exemplary and non-limiting embodiments described herein relate more particularly to devices and surgical procedures pertaining to the cryogenic treatment of uterine tissue to address abnormal uterine bleeding.

Brief Description of Prior Developments

Endometrial ablation is a surgical technique using an operative hysteroscope and is performed as an outpatient procedure to address abnormal uterine bleeding, such as menorrhagia. In such a procedure, the endometrial layers at the inner uterine wall are removed or destroyed such that the opposing walls of the myometrium collapse onto each other and the tissue contracts and develops into a scar. Any endometrium remaining after the ablation is trapped beneath the scar, thus preventing further bleeding.

Global endometrial ablation (GEA) devices utilize different ablation technologies to destroy the endometrium. Such technologies include, for example, the use of radio frequency (RF) energy, cryogenics, thermal energy, or steam. One example of thermal energy is the use of a gaseous medium, such as nitrous oxide, which is released through a nozzle into a uterine conformal balloon at the distal end of the nozzle. The increase in velocity of the gaseous medium flowing through the nozzle, followed by expansion into the uterine conformal balloon, yields cooling temperatures around −85 degrees C. due to the Joule-Thompson Effect. In doing so, an ablation of the uterine tissue is generally completed in about 2 to 3 minutes.

Both traditional endometrial ablation and GEA are used as alternatives to more definitive therapies such as hysterectomy and in instances in which the patient has no desire for future fertility.

SUMMARY

In accordance with one aspect of the invention, a method comprises: providing a medical device comprising a first balloon, a second balloon arranged within the first balloon and having at least one rupture valve, and a fluid-tight intermediary space between the first balloon and the second balloon; inserting the medical device into a uterine cavity; providing a cryogenic agent into the fluid-tight intermediary space; inflating the fluid-tight intermediary space with the cryogenic agent to cause the first balloon to conform to a shape of the uterine cavity; and exhausting the cryogenic agent through the at least one rupture valve and out of the second balloon.

In accordance with another aspect of the invention, a method of performing an endometrial ablation comprises: providing a medical device comprising a shaft having a distal end, a first balloon configured to be attached to the distal end of the shaft, a second balloon configured to be received within the first balloon such that an intermediary space is defined between the first balloon and the second balloon; inserting the medical device into a uterine cavity; providing a gaseous medium into the intermediary space; cycling the gaseous medium through the intermediary space and the second balloon; and ablating uterine tissue at an inner wall of the uterine cavity using an outer surface of the first balloon.

In accordance with another aspect of the invention, a medical device comprises: a shaft having a distal end and an associated exhaust channel; a first balloon configured to be attached to the distal end of the shaft, the first balloon having an outer surface that is substantially conformal to an inner surface of a uterine cavity; and a second balloon configured to be received within the first balloon and forming an intermediary space between the first balloon and an outer surface of the second balloon. The second balloon includes at least one rupture valve configured to rupture at a predefined pressure in the intermediary space.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
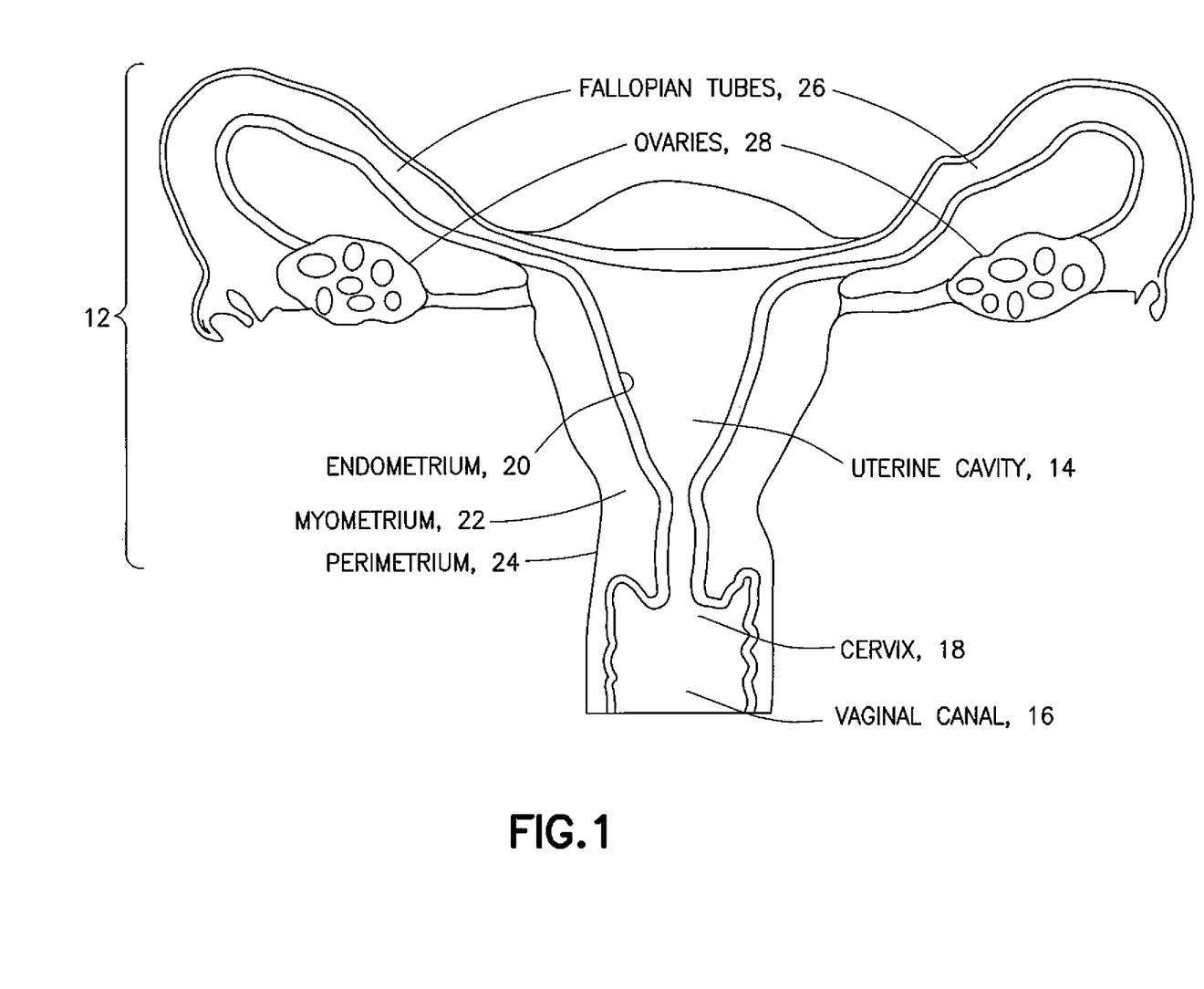
FIG. 1 is a schematic representation of a uterus.

Referring to FIG. 1, a gynecological cavity is shown and designated generally by the reference number 10. The gynecological cavity 10 includes the uterus 12 defining the uterine cavity 14, access to which is generally through the vaginal canal 16 and the cervix 18. The uterine cavity 14 is lined with the endometrium 20, which is a mucous membrane lining the inner uterine wall and which thickens during the menstrual cycle in preparation for possible implantation of an embryo. The endometrium 20 is supported by the myometrium 22 (middle uterine wall). The perimetrium 24 (outer uterine layer) is located on the outer surface of the myometrium 22. The fallopian tubes 26 extend from an upper portion of the uterus 12 and terminate in fimbriated and funnel-shaped openings that wrap partway around the ovaries 28.

Figure 2:
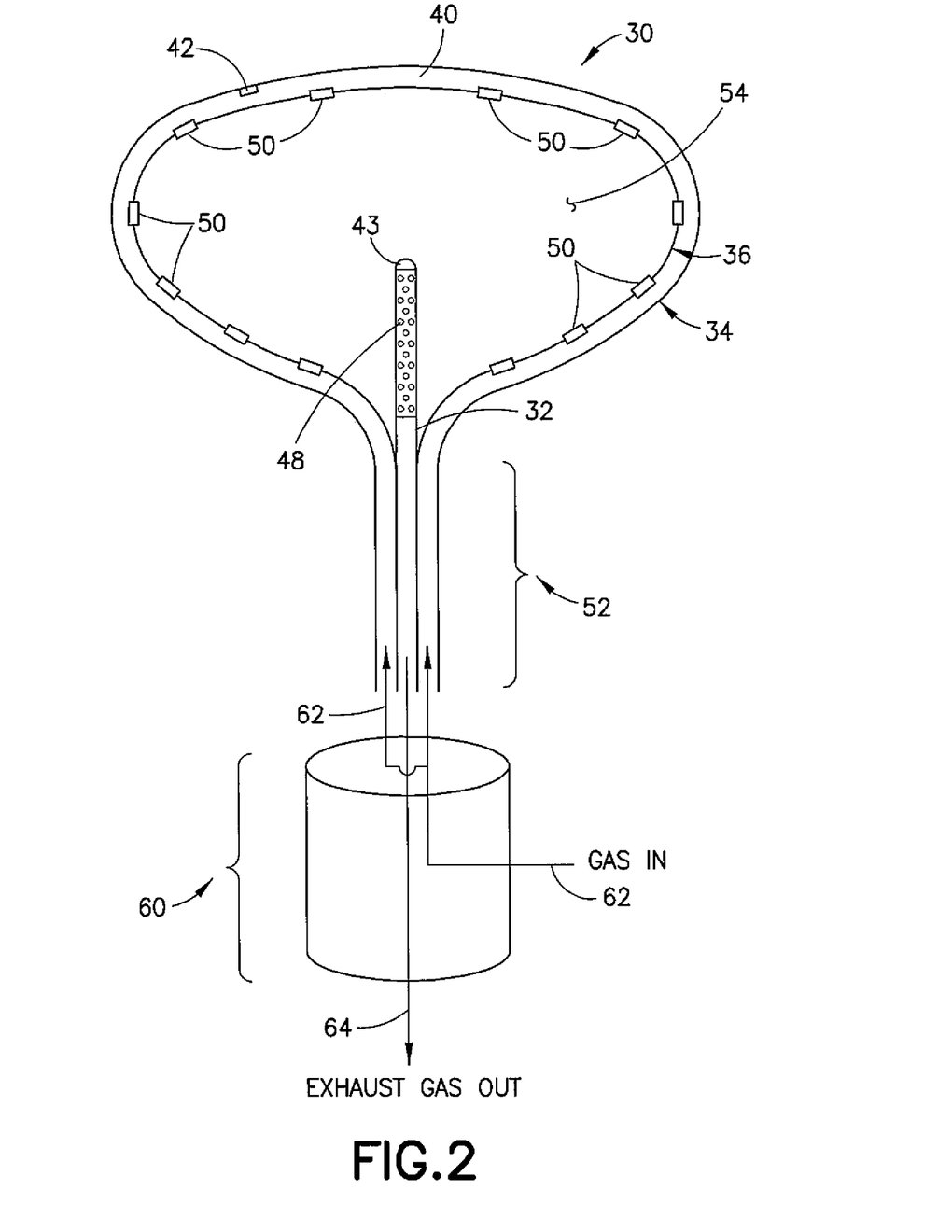
FIG. 2 is a schematic representation of a medical device having a dual-wall balloon for the cryogenic treatment of endometrial tissue using ablation techniques.

Referring to FIG. 2, a medical device for the cryogenic treatment of menorrhagia or other abnormal uterine bleeding using endometrial ablation is designated generally by the reference number 30 and is hereinafter referred to as "device 30." Device 30 may comprise a shaft 32 having a distal end over which a first balloon 34 and a second balloon 36 are mounted, the second balloon 36 being mounted inside the first balloon 34 to form a dual-wall balloon with the second balloon 36 defining an inner wall and the first balloon 34 defining an outer wall with a fluid-tight intermediary volume or space 40 therebetween. A temperature sensor 42 may be mounted on an inner-facing surface of the first balloon 34. The shaft 32 may include a CMOS (complementary metal oxide semiconductor) chip 43 with suitable optic componentry that allows the procedure to be observed. Since the device 30 is disposable, the chip 43 renders the device 30 practical without the need to incorporate an expensive hysteroscope. In the alternative, the shaft 32 may be part of a hysteroscope.

Rupture valves 50 may be located in the inner wall defining the second balloon 36. An inner surface of the second balloon 36 may be attached over an exhaust tube 48 extending along or axially through the shaft 32 of the device 30 and proximate a neck portion 52 of the two balloons such that a distal end of the exhaust tube 48 is received into an inner chamber 54 defined by an inner volume of the second balloon 36. A pressure balance valve 60 may be located in the neck portion 52 with an inlet being through the pressure balance valve 60 and into the space 40 and an outlet being from the inner chamber 54 and through the exhaust tube 48.

To inflate the first balloon 34, a cryogenic agent in the form of a gaseous medium may be introduced into the space 40 (arrow 62) through the inlet of the pressure balance valve 60. To carry out an endometrial ablation (for example, to treat menorrhagia), once the first balloon 34 is inflated, an outward-facing surface of the first balloon 34 may engage the inner uterine wall and substantially conform to the shape of the uterine cavity 14, the rupture valves 50 may rupture at a predetermined pressure and open to allow the gaseous medium to flow from the space 40 to the inner chamber 54, and an exhaust flow of the gaseous medium may be received from the inner chamber 54 through the exhaust tube 48 (arrow 64).

The first balloon 34 may be fabricated from any material configured to suitably cryogenically treat the tissue of the uterine cavity 14 by contacting the endometrium 20 to ablate endometrial tissue. Materials from which the first balloon 34 and the second balloon 36 may be fabricated include, but are not limited to, polyethylenes, polycarbonates, polyimides, and the like, which allow the device 30 to be operated at cryogenic temperatures.

The inner wall defining the second balloon 36 has an outward-facing surface 66 and an inward-facing surface 68 in which the rupture valves 50 are located. In one example embodiment, referring to FIG. 3A, the rupture valves 50 on the second balloon 36 may be flaps 50a. In one embodiment, a flap 50a may be integrally formed with a main body portion of the second balloon 36 along one edge 70 of the flap 50a and structurally weakened along another edge 72 of the flap 50a (for example, by scoring or thinning the material). The flap 50a may be configured such that as the gaseous medium is introduced into the space 40, the integrity of the flap 50a along the edge 72 that is structurally weakened is compromised, and the flap 50a can open to allow the gaseous medium to pass through (arrow 74) and into the inner chamber 54. Once the gaseous medium flows into the inner chamber 54, the gaseous medium may be expelled through the exhaust tube 48.

Figure 3A:
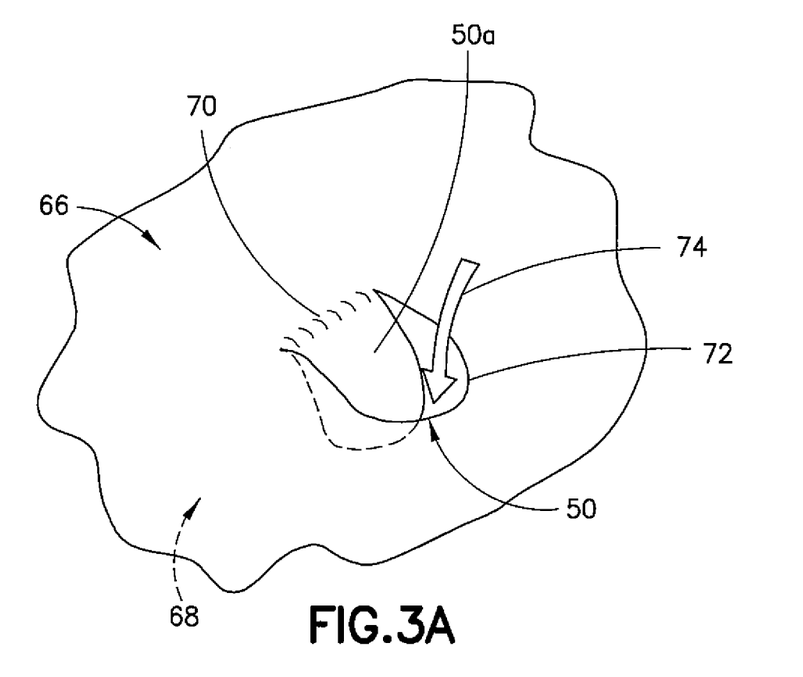
FIG. 3A is a schematic representation of a rupture valve of the balloon of FIG. 2 in which the rupture valve is a selectively-openable flap.
Figure 3B:
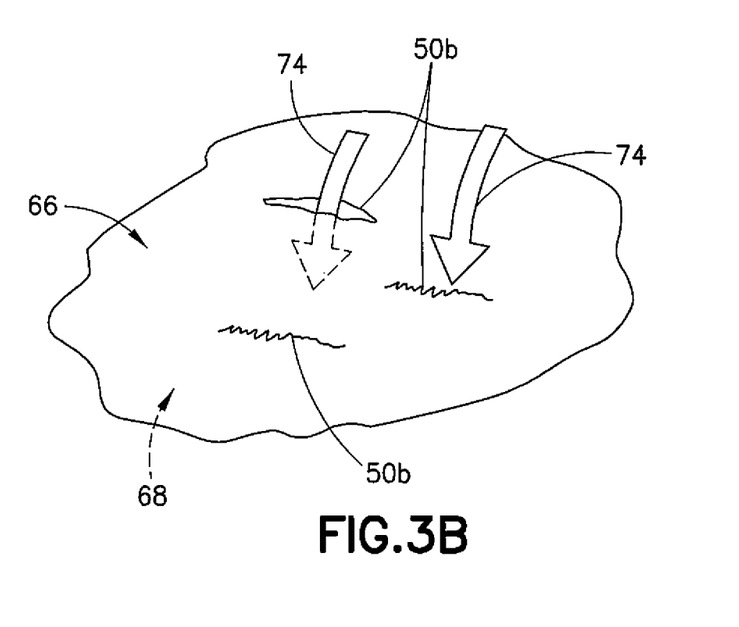
FIG. 3B is a schematic representation of a rupture valve of the balloon of FIG. 2 in which the rupture valve is a selectively-openable structurally weakened closure.

In another embodiment, referring now to FIG. 3B, the second balloon 36 may include slits 50b defined by structurally weakened elongated closures. The structurally weakened elongated closures may be similar to the structurally weakened edges 72 of the flaps 50a. However, upon being compromised, the slits 50b simply open without a "flap" extending into the inner chamber 54. As shown, when the slit 50b is open the gaseous medium (arrow 74) flows therethrough and into the inner chamber 54, whereas when the slit 50b is still closed the gaseous medium is not flowing through. Once the gaseous medium flows into the inner chamber 54, the gaseous medium may be expelled through the exhaust tube 48.

Figure 3C:
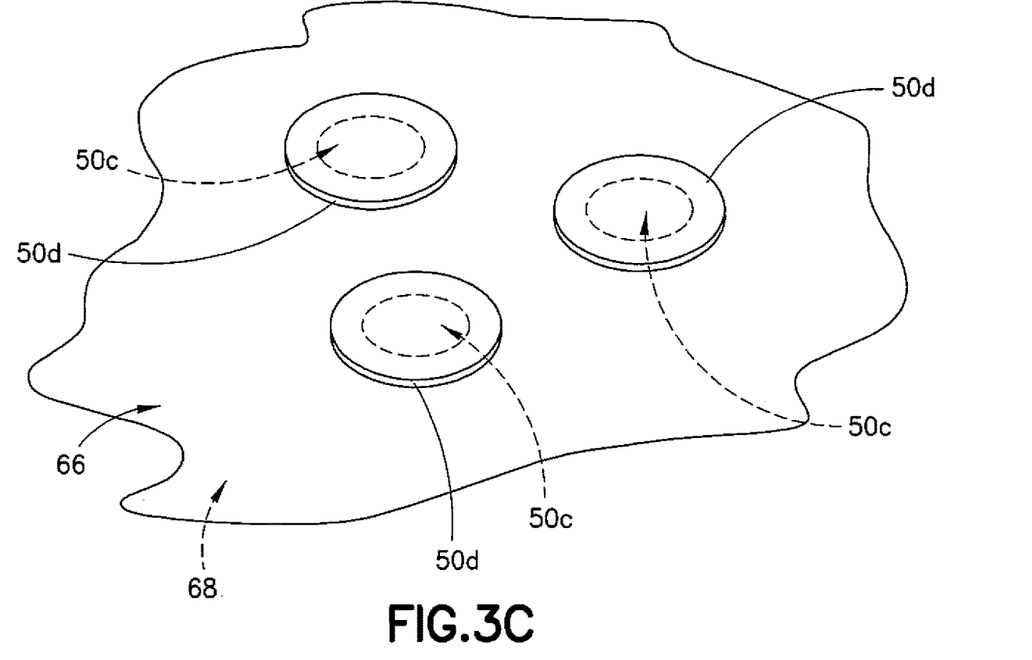
FIG. 3C is a schematic representation of a rupture valve of the balloon of FIG. 2 in which the rupture valve is a selectively-openable hole covered by a removable covering.

In another embodiment, referring now to FIG. 3C, the second balloon 36 may include holes 50c having coverings 50d lightly and removably adhered to the outward-facing surface 66 and covering the holes 50c. The coverings 50d are configured to be blown away from the holes 50c upon introduction of the gaseous medium, which then flows into the inner chamber 54. Once the gaseous medium flows into the inner chamber 54, the gaseous medium may be expelled through the exhaust tube 48.

In any of the foregoing embodiments of the rupture valve 50, because of the low temperatures at which the device 30 is operated, the material of the second balloon 36 may be selected to allow the flaps 50a, the slits 50b, or the holes 50c to be compromised at predetermined pressures.

Figure 4:
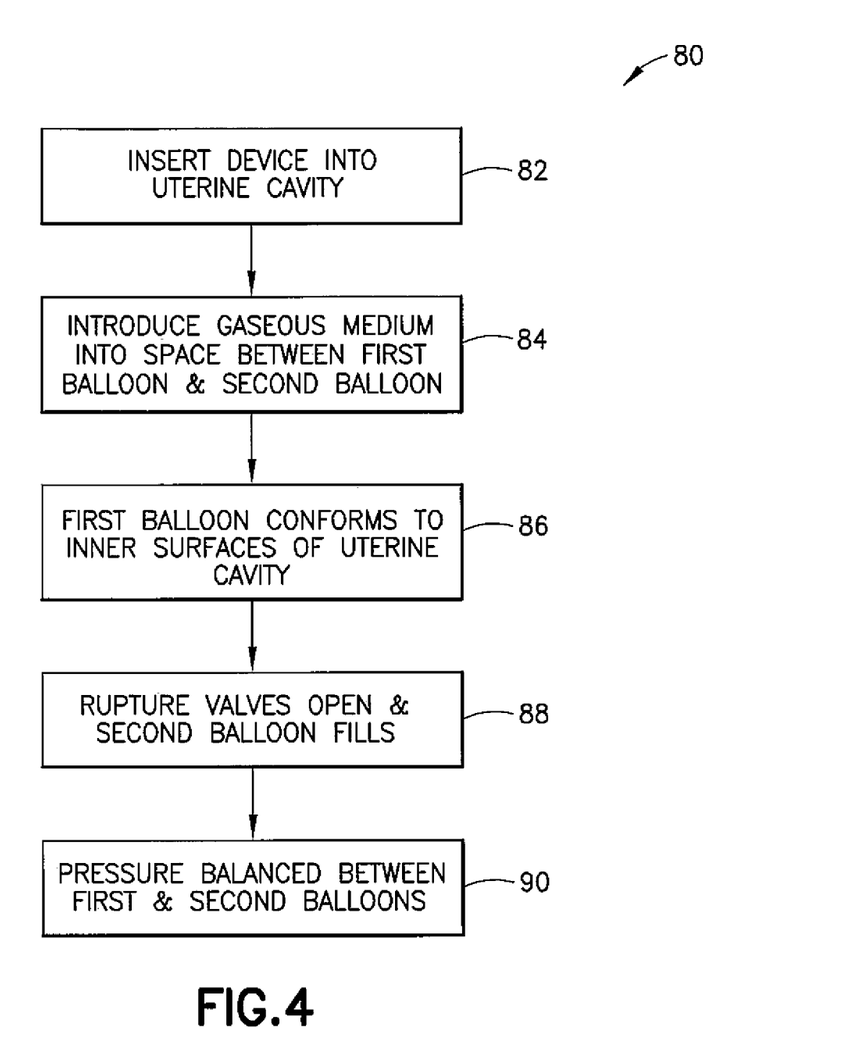
FIG. 4 is a flow of one exemplary embodiment of a method of using a medical device to perform an endometrial ablation.

Referring now to FIG. 4, a flow of one exemplary method of using the device 30 is shown generally at 80 and is hereinafter referred to as "method 80." In method 80, the device 30 with the first balloon 34 and the second balloon 36 in a deflated form is placed over the exhaust tube 48 and the shaft 32 and is trans-cervically inserted into the uterine cavity 14, as indicated at 82. As indicated at 84, a gaseous medium such as nitrous oxide is made to flow through the pressure balance valve 60 and into the space 40 defined by the inward-facing surface of the first balloon 34 and the outward-facing surface 66 of the second balloon 36. At a first predefined pressure that inflates the first balloon 34 via the space 40, the outward-facing surface of the first balloon 34 is configured to be in substantially contiguous contact with the walls of the uterine cavity 14 to carry out the endometrial ablation, as indicated at 86. Once a second predefined pressure (greater than the first predefined pressure) is achieved in the space 40, the rupture valves 50 may be compromised, and the gaseous medium may flow into the inner chamber 54 defined by the second balloon 36, as indicated at 88. Upon the gaseous medium flowing into the inner chamber 54, the first predefined pressure and the second predefined pressure are balanced via the pressure balance valve 60, as indicated at 90, thus allowing for a consistent flow of the gaseous medium into and out of the device 30. Upon achieving a consistent flow of the gaseous medium into and out of the device 30 with contiguous contact of the outward-facing surface of the first balloon 34 with the walls of the uterine cavity 14, thermal energy is transferred to the endometrium 20, which is destroyed at temperatures of about −20 degrees C.

In the method 90, the treatment time is fast since the gaseous medium is cycled into the space 40, maintained for a few seconds, transferred through the rupture valves 50 to the inner chamber 54, and then exhausted through the exhaust tube 48. The pressures are maintained such that the cycle of gaseous medium through the first balloon 34 and the second balloon 36 repeats, thereby allowing fresh gaseous medium to be circulated through the uterine cavity 14 after the thermal energy of the gaseous medium is transferred to the uterine walls.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described below, may be implemented, practiced, or utilized in any combination (for example, any combination that is suitable, practicable, and/or feasible) and are not limited only to those combinations described herein and/or included in the appended claims.

In one aspect, a method comprises: providing a medical device comprising a first balloon, a second balloon arranged within the first balloon and having at least one rupture valve, and a fluid-tight intermediary space between the first balloon and the second balloon; inserting the medical device into a uterine cavity; providing a cryogenic agent into the fluid-tight intermediary space; inflating the fluid-tight intermediary space with the cryogenic agent to cause the first balloon to conform to a shape of the uterine cavity; and exhausting the cryogenic agent through the at least one rupture valve and out of the second balloon.

The method may further comprise balancing a pressure of the cryogenic agent while inflating the fluid-tight intermediary space and while exhausting the cryogenic agent through the at least one rupture valve and out of the second balloon. Balancing a pressure of the cryogenic agent while inflating the fluid-tight intermediary space and while exhausting the cryogenic agent through the at least one rupture valve and out of the second balloon may comprise using a pressure balance valve. Exhausting the cryogenic agent through the at least one rupture valve and out of the second balloon may comprise causing a pressure in the fluid-tight intermediary space to exceed a predefined pressure calculated to maintain a structural integrity of the at least one rupture valve. Providing a cryogenic agent into the fluid-tight intermediary space may comprise introducing nitrous oxide into the fluid-tight intermediary space. Inflating the fluid-tight intermediary space with the cryogenic agent to conform to a shape of the uterine cavity may comprise lowering a temperature at an outer surface of the first balloon to about −20 degrees C. Inflating the fluid-tight intermediary space with the cryogenic agent to cause the first balloon to conform to a shape of the uterine cavity may ablate uterine tissue at a wall of the uterine cavity.

In another aspect, a method of performing endometrial ablation comprises: providing a medical device comprising a shaft having a distal end, a first balloon configured to be attached to the distal end of the shaft, a second balloon configured to be received within the first balloon such that an intermediary space is defined between the first balloon and the second balloon; inserting the medical device into a uterine cavity; providing a gaseous medium into the intermediary space; cycling the gaseous medium through the intermediary space and the second balloon; and ablating uterine tissue at a wall of the uterine cavity using an outer surface of the first balloon.

Providing a gaseous medium may comprise introducing nitrous oxide gas into the intermediary space between the first balloon and the second balloon. Cycling the gaseous medium through the intermediary space and the second balloon may comprise pressurizing the intermediary space between the first balloon and the second balloon, causing a rupture valve in the second balloon to rupture, and exhausting the gaseous medium from the second balloon. Pressurizing the intermediary space, causing a rupture valve to rupture, and exhausting the gaseous medium may comprise balancing a pressure into the first balloon with a pressure out of the second balloon using a pressure balance valve. Ablating uterine tissue at a wall of the uterine cavity using an outer surface of the first balloon may comprise maintaining the outer surface of the first balloon on the wall of the uterine cavity for at least one of a predetermined amount of time and a predetermined temperature. Ablating uterine tissue at a wall of the uterine cavity using an outer surface of the first balloon may comprise lowering a temperature of the outer surface of the first balloon to about −20 degrees C. Ablating uterine tissue at a wall of the uterine cavity using an outer surface of the first balloon may be used to treat menorrhagia.

A medical device comprises: a shaft having a distal end and an associated exhaust channel; a first balloon configured to be attached to the distal end of the shaft, the first balloon having an outer surface that is substantially conformal to an inner surface of a uterine cavity; and a second balloon configured to be received within the first balloon and forming an intermediary space between the first balloon and an outer surface of the second balloon. The ,second balloon includes at least one rupture valve configured to rupture at a predefined pressure in the intermediary space.

The at least one rupture valve may comprise a flap having at least one edge that is integrally formed with a surface of the second balloon and at least one edge that is configured to rupture at a predefined pressure. The at least one rupture valve may comprise a slit defined by a structurally weakened elongated closure. The at least one rupture valve may comprise a hole having a covering removably adhered to an outward-facing surface of the second balloon and covering the hole.

It should be understood that the foregoing description is only illustrative of the invention. Various alternatives and modifications can be devised by those skilled in the art without departing from the invention. Accordingly, the invention is intended to embrace all such alternatives, modifications, and variances which fall within the scope of the appended claims.

What is claimed is:

1. A method comprising:
providing or obtaining a medical device comprising a first balloon, a second balloon arranged within the first balloon and having at least one rupture valve, and a fluid-tight intermediary space between the first balloon and the second balloon;
wherein the at least one rupture valve is configured to rupture in response to at least a predefined pressure being applied to an outer surface of the second balloon;
inserting the medical device into a uterine cavity;
providing an agent into the fluid-tight intermediary space;
inflating the fluid-tight intermediary space with the agent to cause the first balloon to conform to a shape of the uterine cavity; and
exhausting the agent through the at least one rupture valve and out of the second balloon.

2. The method of claim 1, further comprising balancing a pressure of the agent while inflating the fluid-tight intermediary space and while exhausting the agent through the at least one rupture valve and out of the second balloon.

3. The method of claim 2, wherein balancing a pressure of the agent while inflating the fluid-tight intermediary space and while exhausting the agent through the at least one rupture valve and out of the second balloon comprises using a pressure balance valve.

4. The method of claim 1, wherein exhausting the agent through the at least one rupture valve and out of the second balloon comprises causing a pressure in the fluid-tight intermediary space to exceed a predefined pressure calculated to maintain a structural integrity of the at least one rupture valve.

5. The method of claim 1, wherein providing the agent into the fluid-tight intermediary space comprises introducing nitrous oxide into the fluid-tight intermediary space.

6. The method of claim 1, wherein inflating the fluid-tight intermediary space with the agent to conform to a shape of the uterine cavity comprises lowering a temperature at an outer surface of the first balloon to about −20 degrees C.

7. The method of claim 1, wherein inflating the fluid-tight intermediary space with the agent to cause the first balloon to conform to a shape of the uterine cavity ablates uterine tissue at an inner wall of the uterine cavity.

8. The method of claim 1, wherein the at least one rupture valve is offset from a mouth of the second balloon.

9. The method of claim 1, wherein the agent comprises a fluid medium.

10. The method of claim 9, wherein the fluid medium comprises a gaseous medium.

11. A method of performing endometrial ablation, the method comprising:
   providing or obtaining a medical device comprising a shaft having a distal end, a first balloon configured to be attached to the distal end of the shaft, a second balloon configured to be received within the first balloon such that an intermediary space is defined between the first balloon and the second balloon;
   inserting the medical device into a uterine cavity;
   providing a gaseous medium into the intermediary space;
   cycling the gaseous medium through the intermediary space and through a rupture valve into the second balloon; and
   ablating uterine tissue at an inner wall of the uterine cavity using an outer surface of the first balloon.

12. The method of performing endometrial ablation as in claim 11, wherein providing a gaseous medium comprises introducing nitrous oxide gas into the intermediary space between the first balloon and the second balloon.

13. The method of performing endometrial ablation as in claim 11, wherein cycling the gaseous medium through the intermediary space and the second balloon comprises pressurizing the intermediary space between the first balloon and the second balloon, causing a rupture valve in the second balloon to rupture, and exhausting the gaseous medium from the second balloon.

14. The method of performing endometrial ablation as in claim 13, wherein pressurizing the intermediary space, causing a rupture valve to rupture, and exhausting the gaseous medium comprises balancing a pressure into the first balloon with a pressure out of the second balloon using a pressure balance valve.

15. The method of performing endometrial ablation as in claim 11, wherein ablating uterine tissue at an inner wall of the uterine cavity using an outer surface of the first balloon comprises maintaining the outer surface of the first balloon on the inner wall of the uterine cavity for at least one of a predetermined amount of time and a predetermined temperature.

16. The method of performing endometrial ablation as in claim 11, wherein ablating uterine tissue at an inner wall of the uterine cavity using an outer surface of the first balloon comprises lowering a temperature of the outer surface of the first balloon to about −20 degrees C.

17. The method of performing endometrial ablation as in claim 8, wherein ablating uterine tissue at an inner wall of the uterine cavity using an outer surface of the first balloon is used to treat menorrhagia.

18. A medical device comprising:
   a shaft having a distal end and an associated exhaust channel;
   a first balloon configured to be attached to the distal end of the shaft, the first balloon having an outer surface that is substantially conformal to an inner surface of a uterine cavity;
   a second balloon configured to be received within the first balloon and forming an intermediary space between the first balloon and an outer surface of the second balloon;
   wherein the second balloon includes at least one rupture valve configured to rupture at a predefined pressure in the intermediary space establishing an intake port to a volume within the second balloon; and
   an exhaust port configured to allow an exhaust flow to pass from the intake port to the associated exhaust channel via the volume within the second balloon.

19. The medical device of claim 18, wherein the at least one rupture valve comprises a flap having at least one edge that is integrally formed with a surface of the second balloon and at least one edge that is configured to rupture at a predefined pressure.

20. The medical device of claim 18, wherein the at least one rupture valve comprises a slit defined by a structurally weakened elongated closure.

21. The medical device of claim 18, wherein the at least one rupture valve comprises a hole having a covering removably adhered to an outward-facing surface of the second balloon and covering the hole.

22. The medical device of claim 18, wherein the at least one rupture valve is offset from a mouth of the second balloon.

* * * * *

UNITED STATES PATENT AND TRADEMARK OFFICE
CERTIFICATE OF CORRECTION

PATENT NO. : 11,065,150 B2
APPLICATION NO. : 15/924590
DATED : July 20, 2021
INVENTOR(S) : Murdeshwar et al.

It is certified that error appears in the above-identified patent and that said Letters Patent is hereby corrected as shown below:

On the Title Page

Item (57), in "Abstract", in Column 2, Lines 1-10, delete "A medical device includes: a shaft having a distal end and an associated exhaust channel; a first balloon configured to be attached to the distal end of the shaft, the first balloon having an outer surface that is substantially conformal to an inner surface of a uterine cavity; and a second balloon configured to be received within the first balloon and forming an intermediary space between the first balloon and an outer surface of the second balloon. The second balloon includes at least one rupture valve configured to rupture at a predefined pressure in the intermediary space." and insert --Conformal fluid endometrial treatment of uterine tissue can include using nested balloons, i.e., inflating the outer balloon to conform to the uterine cavity, cycling the fluid through an interstitial space between the balloons to treat tissue, and using rupture valves to exhaust fluid from an exhaust port from the inner balloon. Endometrial ablation can include using an inner and an outer balloon capable of fluidic inflation of an interstitial space between the two balloons and further capable of pressure balancing through a plurality of rupture valves and out an exhaust port following conformation of the device to patient anatomy.-- therefor In the Claims In Column 8, Line 11, in Claim 17, delete "8," and insert --11,-- therefor Signed and Sealed this
Sixteenth Day of November, 2021

Drew Hirshfeld
*Performing the Functions and Duties of the
Under Secretary of Commerce for Intellectual Property and
Director of the United States Patent and Trademark Office*